(12) United States Patent
Wagner

(10) Patent No.: US 10,835,359 B2
(45) Date of Patent: Nov. 17, 2020

(54) DENTAL MEASURING INSTRUMENT

(71) Applicant: Global Dental Science, LLC, Scottsdale, AZ (US)

(72) Inventor: Stephen Wagner, Albuquerque, NM (US)

(73) Assignee: Global Dental Science, LLC, Scottsdale, AZ (US)

( * ) Notice: Subject to any disclaimer, the term of this patent is extended or adjusted under 35 U.S.C. 154(b) by 0 days.

(21) Appl. No.: 15/683,453

(22) Filed: Aug. 22, 2017

(65) Prior Publication Data

US 2020/0093582 A1 Mar. 26, 2020

Related U.S. Application Data

(60) Provisional application No. 62/378,204, filed on Aug. 22, 2016.

(51) Int. Cl.
| | | |
|---|---|---|
| *A61C 19/04* | (2006.01) | |
| *A61B 3/11* | (2006.01) | |
| *A61B 5/107* | (2006.01) | |

(52) U.S. Cl.
CPC ............. *A61C 19/04* (2013.01); *A61B 3/111* (2013.01); *A61B 5/1072* (2013.01)

(58) Field of Classification Search
CPC .................................................. A61C 19/04
USPC .................................................. 600/587, 590
See application file for complete search history.

(56) References Cited

U.S. PATENT DOCUMENTS

| | | | |
|---|---|---|---|
| 55,465 A | 6/1866 | Buttles | |
| 90,802 A | 6/1869 | Wuestenberg | |
| 111,429 A | 1/1871 | Boughton | |
| 310,407 A | 1/1885 | Garner | |
| 347,976 A | 8/1886 | Starr | |
| 415,594 A | 11/1889 | Weirich | |
| 429,074 A | 5/1890 | Webb | |
| 1,503,580 A | 8/1924 | Epstein | |
| 1,563,955 A | 12/1925 | Barton | |
| 1,763,553 A | 6/1930 | Dennis | |
| 2,600,899 A | 6/1952 | McClain | |
| 2,817,900 A | 12/1957 | Glasser | |
| 3,234,942 A | 2/1966 | Simor | |
| 3,890,711 A | 6/1975 | Burns | |
| 4,445,854 A | 5/1984 | Bekey et al. | |
| 4,500,289 A | 2/1985 | Garganese | |
| 4,501,556 A | 2/1985 | Zeinigher | |
| 4,530,662 A | 7/1985 | Andersson et al. | |

(Continued)

FOREIGN PATENT DOCUMENTS

| | | |
|---|---|---|
| WO | 199820807 | 5/1998 |
| WO | WO 2015063032 | 5/2015 |

OTHER PUBLICATIONS

Predictable Restorative Excellence With Full and Partial Dentures (2013). (Year: 2013).*

(Continued)

*Primary Examiner* — Etsub D Berhanu

(74) *Attorney, Agent, or Firm* — Derrick Harvey, Harvey Law, PC

(57) ABSTRACT

A device is disclosed for taking critical measurements of a dental patient's anatomical features to aid in building prosthetic teeth in a minimal number of patient visits. The device to a multi-functional tool for dental professionals to acquire valuable anatomical data.

11 Claims, 5 Drawing Sheets

(56) References Cited

U.S. PATENT DOCUMENTS

| | | |
|---|---|---|
| 4,624,639 A | 11/1986 | Wong |
| D289,795 S | 5/1987 | Andersson |
| 4,768,951 A | 9/1988 | Abiru et al. |
| 5,112,225 A | 5/1992 | Diesso |
| 5,554,024 A | 9/1996 | Ueda |
| 5,586,884 A | 12/1996 | Kraus |
| 5,605,459 A | 2/1997 | Kuroda et al. |
| 6,196,840 B1 | 3/2001 | Zentz et al. |
| D555,242 S | 11/2007 | Massad |
| 7,305,990 B2 | 12/2007 | Mathias |
| D671,651 S | 11/2012 | Wagner |
| D673,277 S | 12/2012 | Wagner |
| 8,376,738 B2 | 1/2013 | Wagner |
| 9,326,834 B2 | 5/2016 | Morales et al. |
| 9,707,061 B2 | 7/2017 | Morales et al. |
| 2004/0126731 A1 | 7/2004 | Tucker |
| 2004/0214133 A1 | 10/2004 | Lang |
| 2005/0034733 A1 | 2/2005 | Liddle et al. |
| 2005/0106529 A1 | 5/2005 | Abolfathi et al. |
| 2005/0112523 A1 | 5/2005 | Massad |
| 2006/0105289 A1 | 5/2006 | Wagner |
| 2006/0183080 A1 | 8/2006 | Nosov et al. |
| 2007/0067997 A1* | 3/2007 | Bergman ............... B26B 11/00 30/123 |
| 2007/0231771 A1 | 10/2007 | Kawasaki |
| 2008/0254406 A1 | 10/2008 | Wagner |
| 2009/0246729 A1 | 10/2009 | Massad |
| 2010/0009318 A1 | 1/2010 | Kim |
| 2012/0179281 A1 | 7/2012 | Steigart |
| 2014/0242539 A1 | 8/2014 | Fiskar |
| 2014/0308624 A1 | 10/2014 | Lee |
| 2015/0019176 A1 | 1/2015 | Presswood |
| 2015/0134094 A1 | 5/2015 | Thompson |
| 2015/0230891 A1 | 8/2015 | Grobbee et al. |

OTHER PUBLICATIONS

PCT App PCT/US2017/012058—International Search Report and Written Opinion dated May 11, 2017.

* cited by examiner

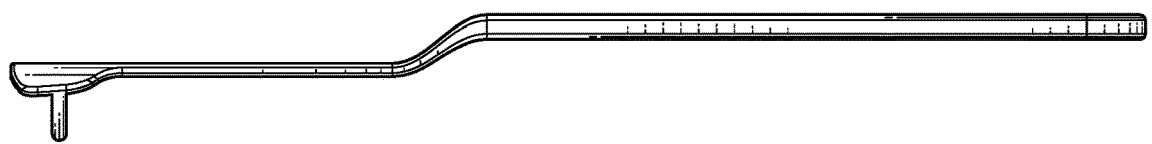
FIG. 3
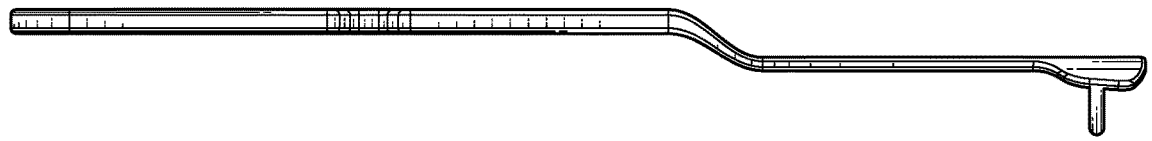
FIG. 4
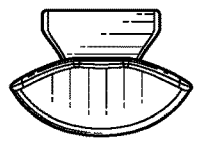     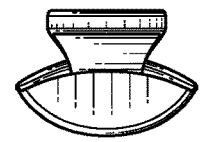
FIG. 5                FIG. 6
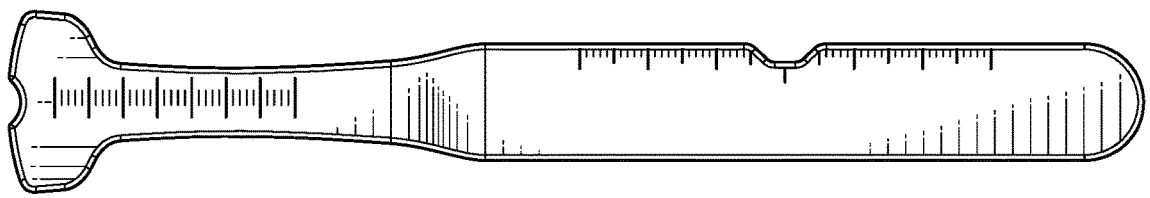
FIG. 7
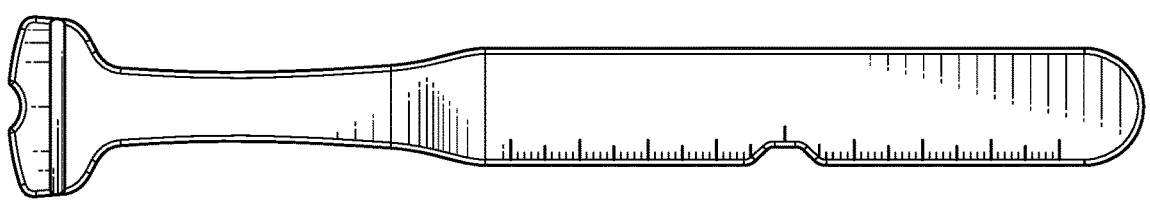
FIG. 8

DENTAL MEASURING INSTRUMENT

RELATED APPLICATION

This application is related to and claims priority from U.S. Provisional Application No. 62/378,204 entitled "Dental Measuring Instrument" filed Aug. 22, 2016, the entire contents of which are hereby fully incorporated herein by reference for all purposes.

FIELD OF THE INVENTION

The present invention relates to dental instruments. The present invention even further relates to taking critical measurements of a dental patient's anatomical features to aid in building prosthetic teeth in a minimal number of patient visits. The present invention even further relates to a multi-functional tool for dental professionals to acquire valuable anatomical data.

BACKGROUND OF THE INVENTION

In the field of aesthetic restorative dentistry, it is desirable to take pre-operative measurements and take high-quality, accurate impressions. In addition, intra-operative measurements are critical in assessing and predicting the aesthetic and functional outcome of the surgical procedure, as well as in the construction of the dental prosthesis. Specifically, the selection of denture teeth is generally understood to be improved when inputting certain dimensional measurements from the patient's anatomy.

One dimensional measurement addresses the positioning of the interdental papilla. A second measurement gauges the distance between the eyes. A third dimensional measurement is the width of the nose and specifically the interalar width. A fourth dimensional measurement helpful for selecting denture teeth is the relationship between the maxillary teeth and the mandibular anterior teeth, both for vertical and horizontal planes used to determining the optimal denture teeth. Other measurements may be found in reference guides known in the arts, such as that published by Panadent Corporation.

There exist a number of different techniques to manage the workflow of a patient seeking dental prosthetic treatments, either sui generis involving dental implantation, with tissue-based prosthetics or in a restorative manner that involves replacement prosthetics.

Managing the time that a patient should spend with a dental professional is a balance, in assuring that the time is effectively spent to acquire all the necessary information to deliver a highly-customized, fully functional final prosthetic.

There exists a need for a method for acquiring vital patient information for delivering final prosthetics that involves fewer visits to the dental professional and less chairside time for both patient and dental professional.

SUMMARY OF THE INVENTION

In accordance with various aspects of the present invention, the invention may comprise a tool for measuring the primary dimensions of a patient's anatomy that aid in selecting denture teeth. An instrument for taking measurements to provide for patient anatomy data, the instrument comprising a first side and a second side, a first end and a second end the first end comprising an indentation at a coronal portion of the first end, the indentation positioned between a first face of the instrument and a second face of the instrument, a first wing and a second wing at the coronal portion of the first end, the first wing and second wing forming a span between the first side and second side, the indentation being positioned at a first face between the first wing and the second wing, a platform positioned between the indentation and a neck of the instrument, the platform extending outwardly from the first face of the instrument, the instrument further comprising a recess disposed between the platform of the first end and the second end, the recess comprising an indentation along the first side of the instrument. The instrument may have a contrasting color along portions of the edge of the tool.

A first appointment where the dental practitioner takes a final impression of the patient's maxilla and/or mandible, uses a papillometer to acquire anatomical measurements of the patient, and select the tooth mould and color that most closely matches the patient, the results of the first appointment producing a first data set, the first data set being utilized to produce a first digital denture that is milled into a first denture base, a second appointment where the dental practitioner seats the first denture base in the patient, the dental practitioner evaluating the tooth position of the first denture base and making adjustments to create a natural smile, and determines the occlusal vertical dimension and records the centric relation, adjusting as necessary, making an interocclusal record with PVS with the first denture base to produce a second data set, the second data set being used to create the final denture, a third appointment where the dental practitioner seats the final denture in the mouth of the patient.

BRIEF DESCRIPTION OF THE DRAWINGS

A more complete understanding of the present invention may be derived by referring to the detailed description and claims when considered in connection with the Figures, where like reference numbers refer to similar elements throughout the Figures, and:

FIG. 3 shows side view of a first side of the inventive instrument.

FIG. 4 shows side view of a second side of the inventive instrument.

FIG. 5 shows an axial view of a first end of the inventive instrument.

FIG. 6 shows an axial view of a second end of the inventive instrument.

FIG. 7 shows a top view of a first face of the inventive instrument.

FIG. 8 shows a top view of a first face of the inventive instrument.

DETAILED DESCRIPTION OF EXEMPLARY EMBODIMENTS OF THE INVENTION

The present invention may be described herein in terms of various components. It should be appreciated that such components may be realized by any number of structural materials and components configured to perform the specified functions. For example, the present invention may be practiced in any number of dental contexts and the exemplary embodiments relating to dental anatomical instrument measurement for the selection of denture teeth are merely a few of the exemplary applications for the invention. For example, the principles, features and methods discussed may be applied to any crown and bridge restorative dentistry or dental and/or oral maxillofacial treatment applications or to other medical applications where a multi-functional dental instrument may be helpful.

Figure 1:
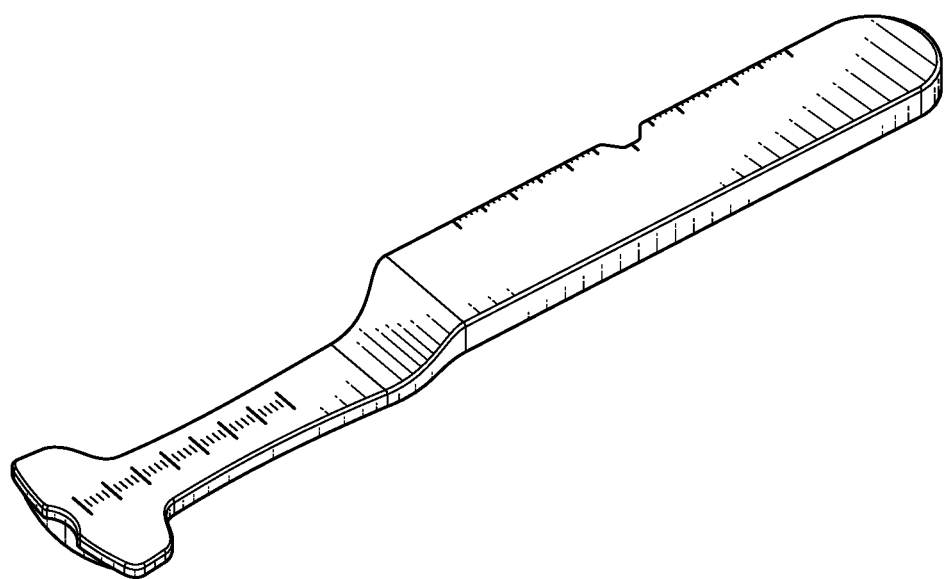
FIG. 1 shows side perspective of a first face of the inventive instrument.

The present invention may be understood in a first embodiment as a device or instrument that aids in taking measurements critical to the fabrication of dental prosthetics in a minimal amount of patient interactions. In accordance with an exemplary embodiment, a multi-functional dental instrument may comprise a first end and a second end, the first end being suitable for a papillameter for measuring maxially lip length and high line smile by use of a ruler that may measure a number of unit measurements from the first end towards the second end. The unit measurements may be customized for regional preference or use of metric vs. English units. The coronal portion, as embodiments of the invention in FIGS. 1-2 indicate, may further include a first face and a second face both of which may include the measurements described infra. The inventive instrument may further include a body at the second end, and a neck between the first end and the body.

Figure 9:
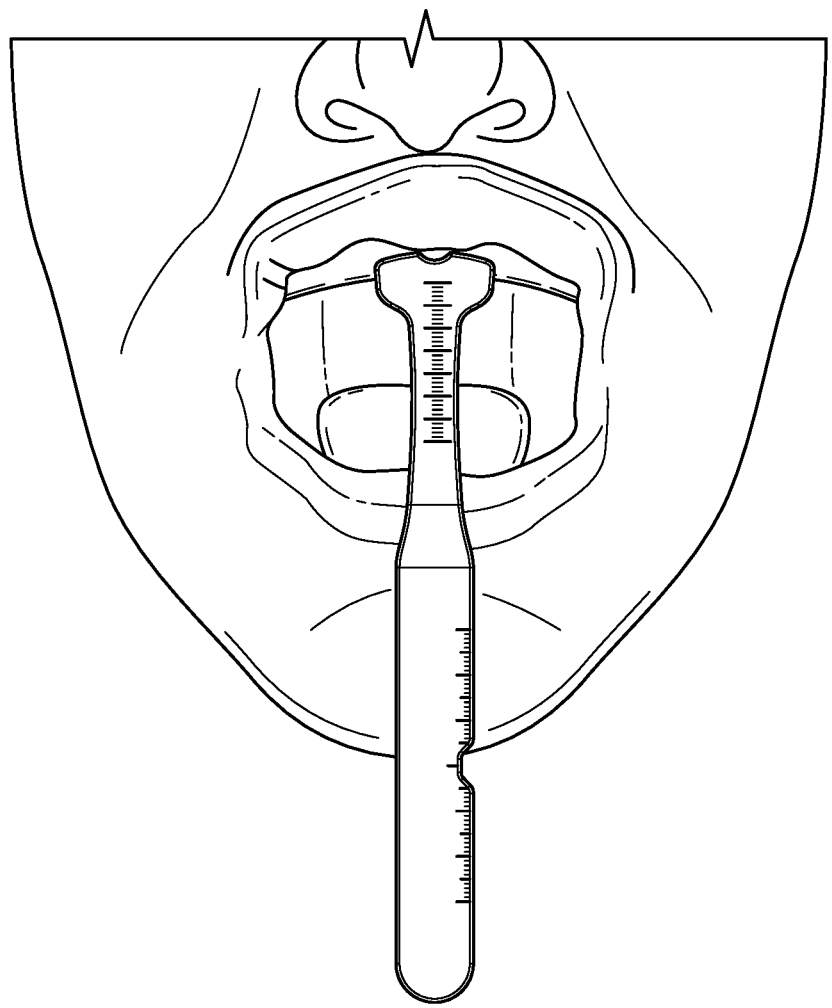
FIG. 9 shows a view of the inventive tool as deployed in the patient's mouth.
Figure 10:
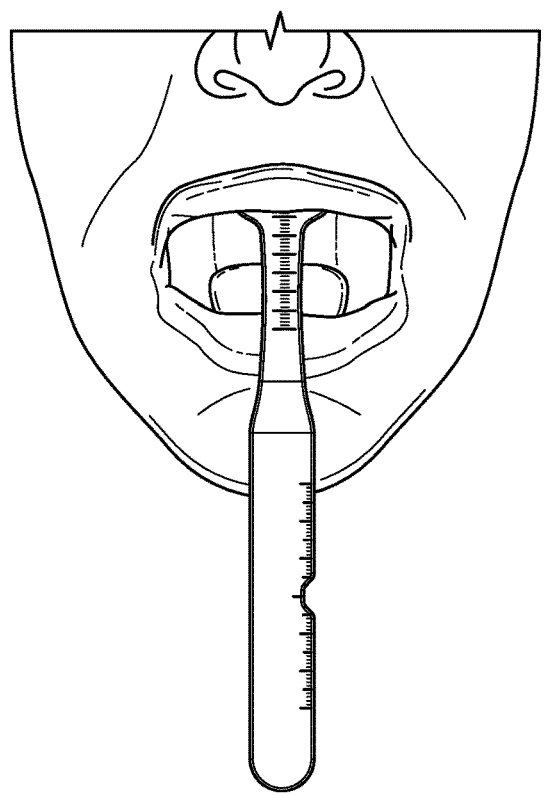
FIG. 10 depicts a front view of the inventive instrument being utilized to record the length of the upper lip.
Figure 11:
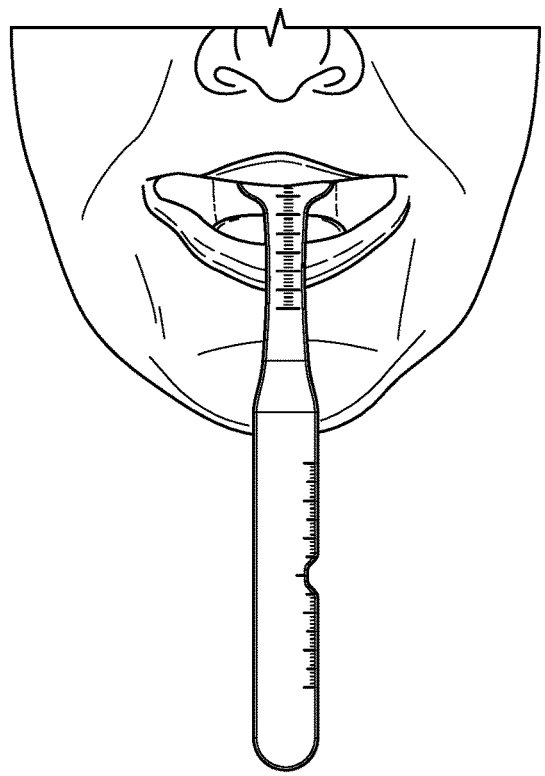
FIG. 11 depicts a similar front view as FIG. 10, but with the inventive instrument recording the high smile line.
Figure 12:
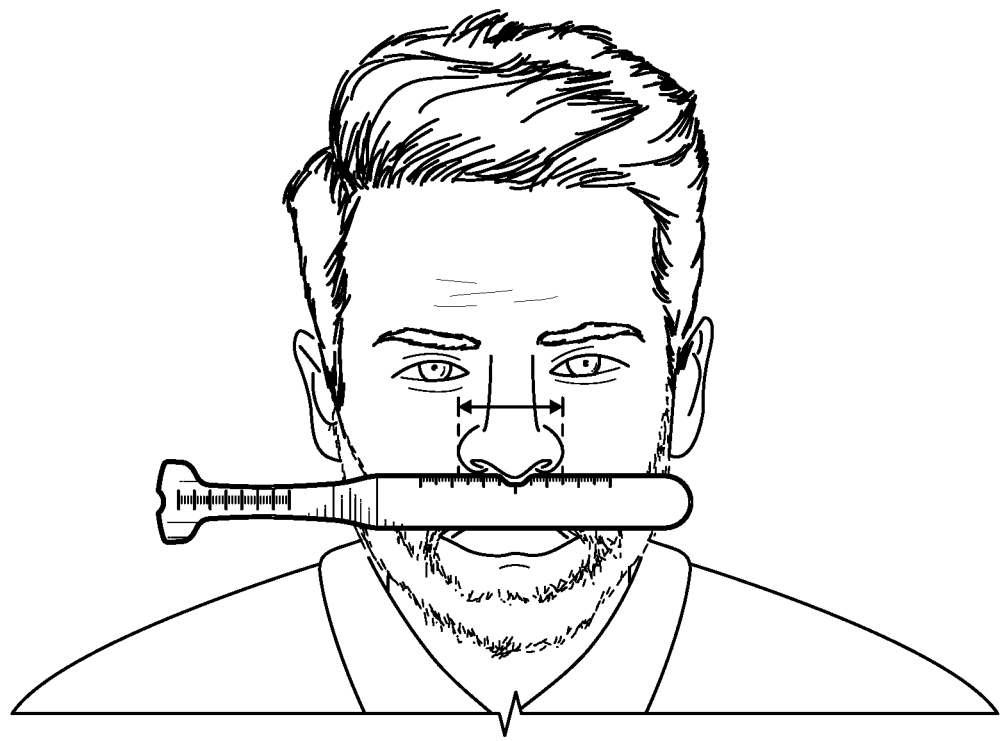
FIG. 12 depicts a front view of the inventive instrument being used to record the max dimension of the ala of a dental patient.
Figure 13:
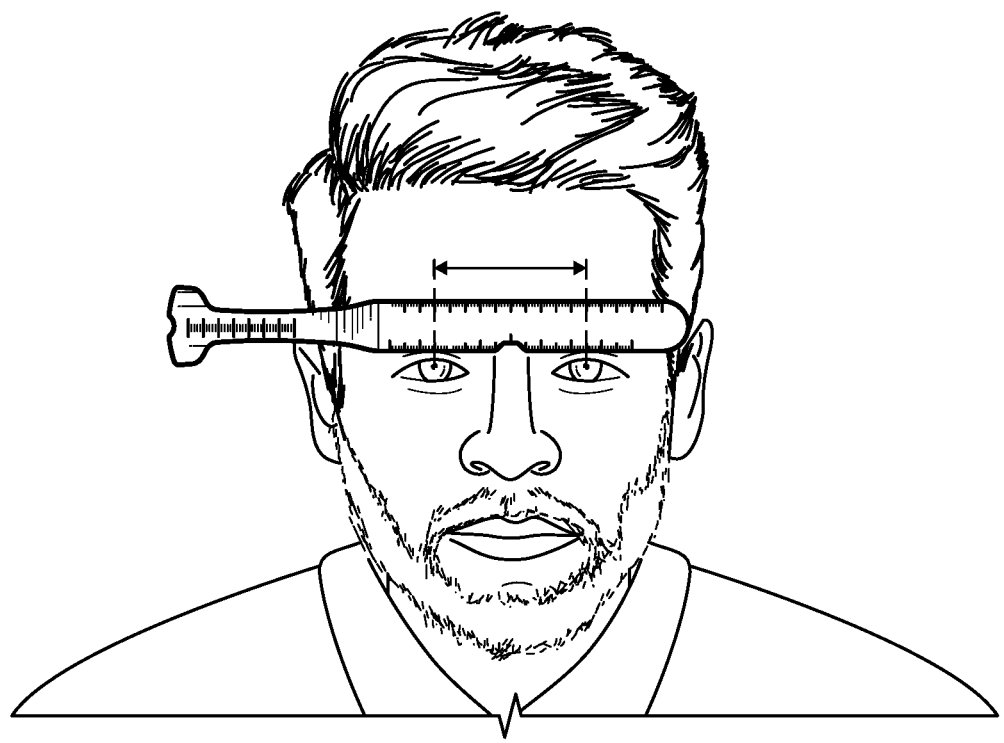
FIG. 13 depicts a front view of the inventive instrument being utilized to record the interpupillary dimension of a patient.

The first end may further comprise, according to FIGS. 2-6, a coronal portion and a base portion. The coronal portion may comprise an indentation at the first end, the indentation extending from a first side to a second side, creating a cutout portion in the first and second face. Though indentation is shown as extending between the first and second face, the cutout portion of indentation may be understood in other embodiments not shown as being positioned only in the first or second face of the instrument. As shown in FIG. 9, indentation may engage the papilla of the patient, Looking more closely at FIGS. 7-8, the cut-out portion of indentation may resemble a semi-circle, and other embodiments of the invention include other geometrical designs that may engage a protruding papilla bulb emerging from the gingiva, such as designs with additional curved and/or linear portions. According to FIG. 2, indentation may have a width as viewed from the first face to the second face, the width being less than other portions of the instrument. In other embodiments, indentation may comprise a width that is sized to approximate the average protrusion of a human papilla, as understood by those skilled in the arts. In still other embodiments, instruments may include different sizes such as small-medium-large that have correlating width of the indentation.

Looking further at embodiments shown in FIGS. 2-6, the first end of the instrument may comprise a first wing and second wing of the instrument positioned on a first side and second side of the inventive instrument. FIG. 7 specifically shows the indentation as being disposed between the first wing and second wing, so that the first and second wing together create a span that extends toward a neck of the instrument, the span having a perimeter at its outermost margin. In embodiments of the invention, span may comprise a perimeter that includes the indentation.

In an embodiment of the instrument, the base portion of the coronal end may comprise a platform illustrated in FIGS. 2-6 as having a parabolic structure having approximately a perpendicular orientation with the majority of the first face of the instrument. The parabolic structure of the platform, by way of example and not limitation, is shown as a semi-circle. Platform may be positioned between the indentation and the second end of the instrument, and appropriate for engaging the maxillary ridge of a patient's gingiva. In embodiments shown in FIGS., the platform may be positioned between the first wing and second wing. In other embodiments, platform may be positioned along other portions of the first end. The portions of span proximal to the indentation may represent an apex of the instrument and may taper back toward a center of a face of the instrument to the neck of the instrument.

In another embodiment of the invention, the perimeter of span may include a biased portion that tapers toward the platform, creating a bowl effect about the coronal portion of the instrument. In this embodiment, platform may form a junction with the span at the face of the instrument that is parabolic, though platform may continue to exist in a perpendicular relationship with other portions of the first and/or second face of the instrument.

Between the first end and the second end and at the first face and/or second face, the instrument may comprise a flattened profile. The instrument may comprise at least one non-linear aspect, as shown in FIGS. 1-4. In the embodiment shown in FIG. 2, the non-linear aspect of the instrument is disposed towards the face of the instrument that includes the platform, so that first end of the instrument comprises a parallel but separate altitude from the second end. The non-linear aspect is shown to extend between the body and neck of the instrument. Other locations of the non-linear aspects of the instrument may be utilized, including along other portions of the device within the scope of the invention. Furthermore, other embodiments of the instrument may include additional non-linear aspects not shown in the illustrations are within the scope of the present invention.

Figure 2:
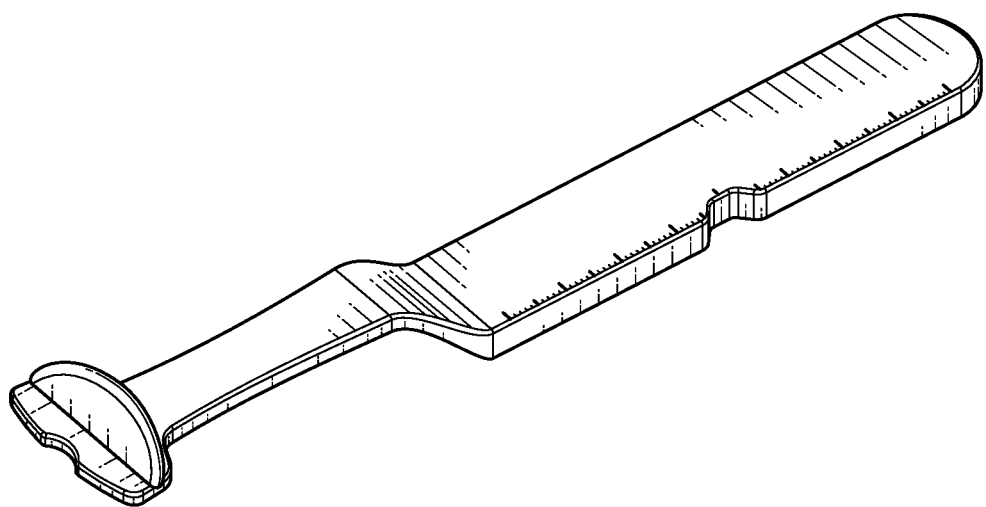
FIG. 2 shows side perspective of a second face of the inventive instrument.

Moving on towards the second end, FIG. 2 indicates a linear aspect of the device that may comprise a recess at the first side, the recess having ruler marks on one or both sides extending towards the first end and/or the second end. The recess may have a number of different geometric configurations according to different embodiments of the invention. The recess shown in FIGS. 1 and 2 include a center element that may resemble half of a hexagon, with rounded intersections. Other examples of the recess may resemble geometric configurations capable of fitting a nasolabial angle, especially those resembling an alameter used in the arts of dental measuring tools, such as an alameter capable of measuring the interpupillary distance of a patient. In an embodiment not shown in the illustrations, the perimeter of device may be equipped with a bright color to verify on a horizontal plane the device's parallel to inter-pupillary line when measuring the width of nose from alae to ala. The overall length of the device from the first end to the second end may extend from 0 to 30 mm on either side of the center element in an embodiment of an invention, or to ranges greater or smaller than that distance. The center element of the recess may be used to place against the incisal edge of a central (dentate or denture) tooth to determine and verify length and width of existing tooth. On the opposite face of the device, a facial measuring rule may extend from on the linear aspect of the device. The facial rule may estimate the total width of the patient's six anterior teeth.

According to FIG. 2, recess may have a width as viewed from the first face to the second face, the width being less than other portions of the instrument. In other embodiments, recess may comprise a width that is sized to approximate the average protrusion of a human papilla, as understood by those skilled in the arts. In still other embodiments, instruments may include different sizes such as small-medium-large that have correlating width of the indentation.

In an embodiment of the invention, the second end may be capable of measuring an anterior tooth, or the relationship between the maxillary and mandibular anterior teeth in both the horizontal and vertical planes. In the embodiment not shown the second end may be arranged with a rule for measuring along a perpendicular plane, and along a parallel plane extending between the first and second ends.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims.

The invention claimed is:

1. An instrument for taking measurements to provide for patient anatomy data, the instrument comprising:
   a first side and a second side;
   a first end and a second end, the first end comprising:
      an indentation at a coronal portion of the first end, the indentation positioned between a first face of the instrument and a second face of the instrument;
      a first wing and a second wing at the coronal portion of the first end, the first wing and second wing forming a span between the first side and second side, the indentation being positioned at a first face between the first wing and the second wing; and
      a platform positioned between the indentation and a neck of the instrument, the platform extending outwardly from the first face of the instrument;
   the instrument further comprising a recess disposed along the first side of the instrument between the platform and the second end, the recess having a center element and ruler markings that extend from the center element towards the first end and from the center element toward the second end; and
   the instrument further comprising a non-linear aspect positioned between the platform and the second end, the recess being positioned between the non-linear element and the second end.

2. The instrument of claim 1 further comprising a body portion towards the second end and a neck portion between the first end and the body portion, the non-linear aspect extending between the neck portion and the body portion.

3. The instrument of claim 2, the non-linear aspect disposing the first end of the instrument to a different altitude than the second end of the instrument, whereby the first end remains parallel to the second end.

4. The instrument of claim 1, whereby the indentation has a curved portion at the first face or the second face and extends between the first face and the second face.

5. The instrument of claim 4, the platform having an open end opposite that of the first face, the open end having a curved aspect.

6. The instrument of claim 5, whereby the open end further comprises a circumferential boundary.

7. The instrument of claim 1, whereby the span curves away from the first face of the instrument, and whereby the first wing at the first side and the second wing at the second side are biased away from the first face of the instrument.

8. The instrument of claim 1, whereby the span further comprises a perimeter at the first end, and whereby the perimeter tapers toward the platform.

9. The instrument of claim 1, whereby the recess resembles a half-hexagon having rounded corners.

10. The instrument of claim 1, whereby the recess has graduated markings that extend towards the first side and towards the second side.

11. The instrument of claim 1 further comprising a contrasting color along portions of the first side or the second side of the instrument.

* * * * *